United States Patent [19]

Patapoff et al.

[11] Patent Number: 5,656,246
[45] Date of Patent: Aug. 12, 1997

[54] CONTAMINANT DESTRUCTION BY OXIDATION PROCESSING VIA ENHANCED OZONATION

[75] Inventors: Walter Patapoff, San Dimas; Patricia A. Stoots, Mountain Center, both of Calif.

[73] Assignee: International Ecoscience, Inc., Santa Ana, Calif.

[21] Appl. No.: 550,082

[22] Filed: Oct. 30, 1995

[51] Int. Cl.⁶ .................................................. B01J 8/00
[52] U.S. Cl. ................ 422/187; 422/110; 422/120; 422/186.07
[58] Field of Search .................. 422/187, 120, 422/123, 186.07, 186.08, 186.1, 186.12, 186.14, 305, 2, 28, 110, 115; 426/332

[56] References Cited

U.S. PATENT DOCUMENTS

| | | | |
|---|---|---|---|
| 4,375,812 | 3/1983 | Vaseen et al. | 128/207.27 |
| 4,485,519 | 12/1984 | Collier | 15/359 |
| 4,549,477 | 10/1985 | McCabe, Jr. | 99/477 |
| 4,796,311 | 1/1989 | Shankman | 4/596 |
| 4,849,237 | 7/1989 | Hurst | 426/332 |
| 4,988,484 | 1/1991 | Karlson | 422/186.19 |
| 5,011,699 | 4/1991 | Mitsuda et al. | 426/320 |
| 5,053,339 | 10/1991 | Patel | 436/2 |
| 5,069,880 | 12/1991 | Karlson | 422/186.19 |
| 5,097,556 | 3/1992 | Engel et al. | 8/158 |
| 5,179,943 | 1/1993 | Hama et al. | 128/368 |
| 5,181,399 | 1/1993 | Engel et al. | 68/13 R |
| 5,188,099 | 2/1993 | Todeschini et al. | 128/205.26 |
| 5,205,927 | 4/1993 | Wickramanayake et al. | 210/170 |
| 5,207,737 | 5/1993 | Hanley et al. | 137/85 |
| 5,236,673 | 8/1993 | Coakley et al. | 422/186.07 |
| 5,241,720 | 9/1993 | Engel et al. | 8/158 |
| 5,245,845 | 9/1993 | Langford | 68/3.055 |
| 5,266,275 | 11/1993 | Faddis | 422/116 |
| 5,403,602 | 4/1995 | Endico | 426/231 |
| 5,404,732 | 4/1995 | Kim | 68/13 R |
| 5,409,616 | 4/1995 | Garbutt et al. | 210/760 |
| 5,478,533 | 12/1995 | Inculet | 422/186.07 |
| 5,520,888 | 5/1996 | Berndt | 422/186.08 |

OTHER PUBLICATIONS

*Meat & Poultry*, "Evaluating Reduction Technologies", Dr. Amy Waldroup, pp. 10 and 68, Aug. 1995.

*Primary Examiner*—Christopher Kim
*Attorney, Agent, or Firm*—Aquilino & Welsh

[57] ABSTRACT

A system for enhanced contaminant destruction through the use of oxidation processing. The system includes a contacting process chamber where ozone is solubilized into a solvent to create ozonated solvent and an oxidation processing chamber coupled to the contacting process chamber which selectively supplies ozonated solvent to the oxidation processing chamber. The system further includes an ozone generator coupled to the contacting process chamber and the oxidation processing chamber to selectively supply ozone to either chamber. A gas treatment system is coupled to the contacting process chamber and the oxidation processing chamber to treat gases produced in the contacting process chamber and the oxidation processing chamber for destruction or reuse, wherein the gas treatment system is selectively in fluid communication with the contacting process chamber and the oxidation processing chamber. In addition, a solvent/water treatment system is coupled to the contacting process chamber and the oxidation processing chamber to treat waste produced in the contacting process chamber and the oxidation processing chamber for reuse, wherein the solvent/water treatment system is selectively in fluid communication with the contacting process chamber and the oxidation processing chamber.

20 Claims, 1 Drawing Sheet

CONTAMINANT DESTRUCTION BY OXIDATION PROCESSING VIA ENHANCED OZONATION

BACKGROUND OF THE INVENTION

1. Field of the Invention

The invention relates to a system for decontamination and/or remediation. More particularly, the invention relates to a system using ozone and/or other oxidants in the decontamination and/or remediation of a variety of contaminated solids, liquids or gases.

2. Description of the Prior Art

Conventional decontamination or remediation methods and apparatuses produce a wide variety of undesirable byproducts and/or secondary wastes. Additionally, prior methods and apparatuses are limited in their ability to fully decontaminate the objects to which they are applied. For example, conventional laundering processes utilize hot water, detergents, brighteners, bleach and other additives. Commercial laundering processes additionally apply souring steps and numerous rinsing steps. The water used during laundering is often discharged after a single use, thus ineffectively conserving resources.

Currently, humans take showers in an open loop system which is very ineffective in conserving water resources. This is especially worrisome when individuals are confined to environments where clean water is not readily available for showering and decontamination against chemical or biological agents. For example, water supplies are generally limited during space flight, in submarines and other ships, and during combat. In addition, clean water supplies are often difficult to locate in remote locations and underdeveloped countries. This lack of potable water often leads to disease, affecting vast portions of certain populations.

Conventional soap and water showers are also limited in their ability to kill bacteria. Specifically, soap may not effectively reach and cleanse all body parts. For example, a typical soap and water shower may not effectively attack bacteria residing on the surface of the skin, under fingernails, in body crevices or orifices, and in the hair. The open loop nature of a conventional showers also does not reduce the likelihood of the spread of bacteria, viruses, and disease. Further, conventional showers are not able to deodorize humans, and, therefore, individuals must rely on other means for deodorizing themselves.

Dishwashing is another common process where decontamination is important. Dishwashing produces many of the problems found in laundering and showering. For example, dishwashing produces undesirable run-offs and requires substantial water resources. Additionally, dishwashing processes are consistently confronted with deposits causing water spots on dishes.

Meat, raw vegetable and raw fruit products processing also require decontamination to remove dirt, pesticide and herbicide residues, and pathogenic organisms before the products can be shipped for public consumption. Meat requires decontamination for the removal of enterobacteriaceae, such as, *escherichia coli*, salmonella spp. and enterobacteria spp. Chlorine treatment has been used to decontaminate meats for some time, although chlorine treatment is known to have only limited effectiveness. Similarly, fruits and vegetables must be decontaminated to remove contaminants such as pesticides, bacteria and other harmful materials.

Recently, ozone has been used to treat meat and other foodstuff. However, prior patents fail to disclose a viable process or system for the application of ozone in the treatment of meat, raw vegetables and fruit.

While a few applications for the use of ozone as a decontamination/remediation material are discussed above, it should be understood that ozone is known to be used in a wide variety of applications.

In view of the shortcomings of prior decontamination/remediation methods and apparatuses, a need exists for an effective decontaminating/remediating system which limits chemical run-offs, conserves resources, and fully decontaminates objects.

SUMMARY OF THE INVENTION

It is, therefore, an object of the present invention to provide a system and process for decontamination and/or remediation of a variety of solids, liquids and gases.

Accordingly, the present invention provides a system for enhanced contaminant destruction through the use of oxidation processing. The system includes a contacting process chamber where ozone is solubilized into a solvent to create ozonated solvent and an oxidation processing chamber coupled to the contacting process chamber which selectively supplies ozonated solvent to the oxidation processing chamber. The system further includes an ozone generator coupled to the contacting process chamber and the oxidation processing chamber to selectively supply ozone to either chamber. A gas treatment system is coupled to the contacting process chamber and the oxidation processing chamber to treat gases produced in the contacting process chamber and the oxidation processing chamber for destruction or reuse, wherein the gas treatment system is selectively in fluid communication with the contacting process chamber and the oxidation processing chamber. In addition, a solvent/water treatment system is coupled to the contacting process chamber and the oxidation processing chamber to treat waste produced in the contacting process chamber and the oxidation processing chamber for reuse, wherein the solvent/water treatment system is selectively in fluid communication with the contacting process chamber and the oxidation processing chamber.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
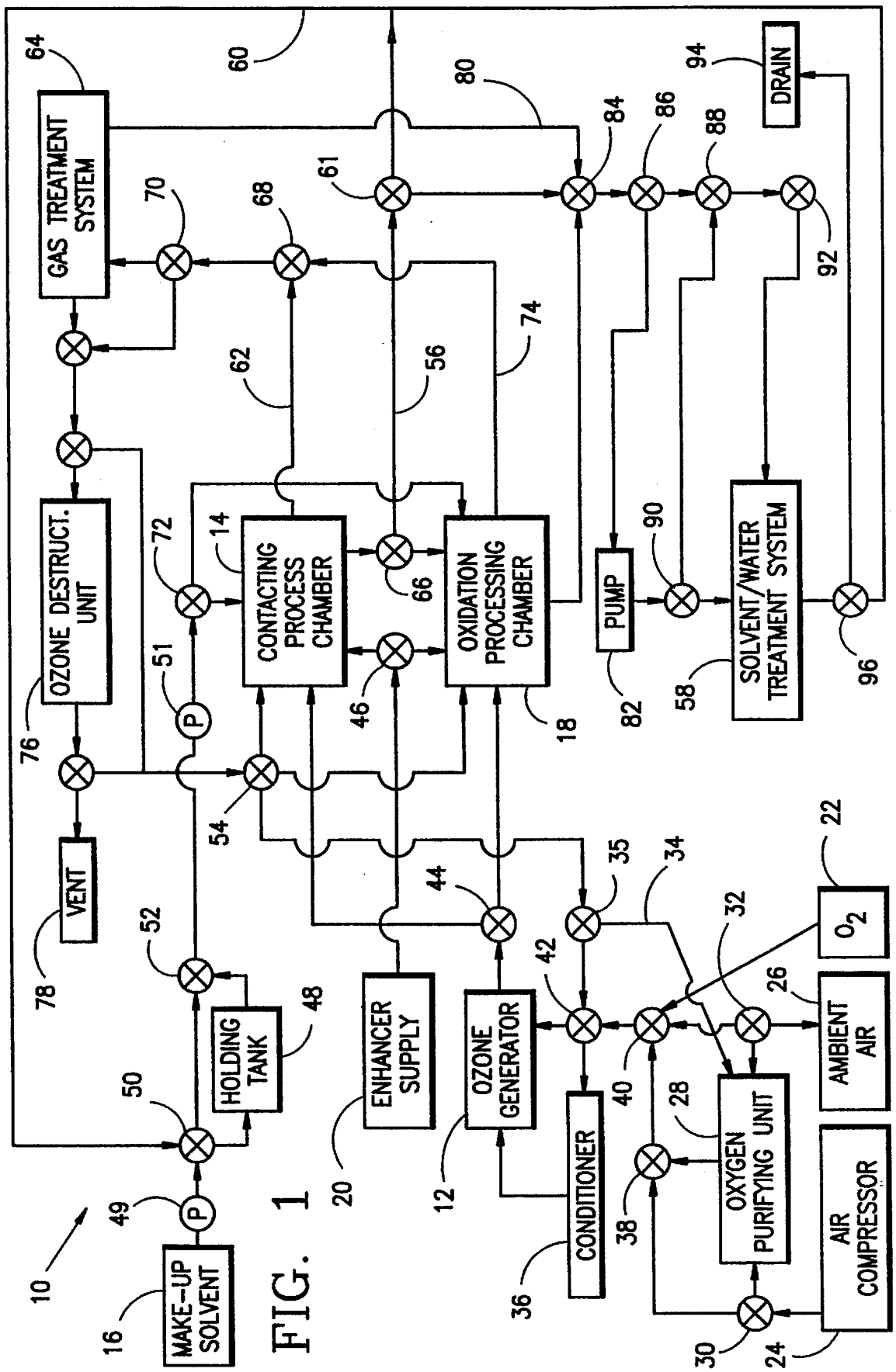
FIG. 1 is a schematic representation of the decontamination and/or remediation process.

The detailed embodiment of the present invention is disclosed herein. It should be understood, however, that the disclosed embodiment is merely exemplary of the invention, which may be embodied in various forms. Therefore, the details disclosed herein are not to be interpreted as limited, but merely as the basis for the claims and as a basis for teaching one skilled in the art how to make and/or use the invention.

Briefly, with reference to FIG. 1, the system 10 begins with a feed stream containing oxygen. The feed stream is coupled to an ozone generator 12 for the production of ozone. The generated ozone gas may be fed to a contacting process chamber 14 for solubilizing the ozone into a make-up solvent 16 for liquid phase oxidation processing. If ozone is to be used for oxidation in the vapor phase, it may be directly introduced into the oxidation process chamber 18 for the purpose of decontamination and/or remediation of the target substrate(s) or contaminated solution (i.e., waste water treatment). Before commencement of the oxidation processing step, oxidation enhancers 20 and substrate(s) are placed within the oxidation process chamber for batch processing or made available to the system for semi-continuous or continuous processing. Once oxidation processing is completed, the resultant gas and liquid streams are separated for further treatment and reuse within the system 10, or for disposal purposes.

More specifically, the present decontaminating and/or remediation system 10 is disclosed. The system begins with the development of ozone in an ozone generator 12. The ozone generator(s) 12 may use corona discharge, cold cathode or ultraviolet methods for the production of ozone. Other known methods, or combinations thereof, may also be employed for the purpose of generating an appropriate quantity of ozone, without departing from the spirit of the present invention.

Oxygen is supplied to the ozone generator 12 from a variety of sources. Specifically, pure oxygen 22 may be supplied directly to the ozone generator. Other sources of oxygen may include an air compressor 24 or ambient air 26. When either compressed air 24 or ambient air 26 is supplied to the ozone generator 12, the air may be treated by an oxygen purifying unit 28, or air separation or oxygen generation unit, to maximize the oxygen in the feed stream provided to the ozone generator 12. This stream may also contain up to 10% Nitrogen which may enhance the effects of ozone production. Flow of the air from the air compressor 24 and the ambient air 26 to the oxygen purifying unit 28 is respectively controlled by valves 30 and 32.

Recycled air 34 coming from the contacting process chamber 14 may also be supplied to the ozone generator 12. The recycled air 34 is selectively passed either directly to the ozone generator 12 or to the oxygen purifying unit 28 or the conditioner 36 prior to being passed to the ozone generator 12. Control of the recycled air 34 is provided by valve 35 and valve 42.

Whether the air is supplied as oxygen, compressed air, ambient air, or recycled air from the contacting process chamber 14, the feed stream may be passed through a conditioner 36, to provide a stream with a dew point in the range of 50° F., prior to entering the ozone generator. Air conditioned in this manner will optimize the production of ozone by the ozone generator 12. The flow of air going to the conditioner 36 and ozone generator 12 is controlled by a series of valves 35, 38, 40, and 42.

The ozone generated by the ozone generator 12 can be split at valve 44 and transported to either the contacting process chamber 14 or oxidation processing chamber 18. Similarly, an enhancer 20 is selectively supplied to either or both the contacting process chamber 14 and the oxidation processing chamber 18 through valve 46. Enhancement of the oxidation process may include any and all components which contribute oxidizing characteristics to effect controlled or uncontrolled reaction with substrate contaminants. Enhancers may include any additive agent which promotes, initiates or inhibits ozone or generates oxidation mechanisms. For example, additive oxidants may include but are not limited to, ultraviolet (UV) radiation,. ultrasound, hydrogen peroxide, ozone, ozone+UV, ozone+$H_2O_2$, ozone+$MnO_2$-coated polystyrene foam, ozone+$MnO_2$, coated activated carbon, Fenton's reagent ($H_2O_2$+$Fe^{-2}$), hydrogen peroxide ($H_2O_2$, alone), activated ceramic disks, ozone+$ZnSO_4 \cdot 7H_2O$, etc. including unstated agents or combinations thereof. Additive oxidant oxidizing potentials can range from 0.5 to 3.0 volts at 25° C.

With regard to the contacting process, ozone is solubilized into an aqueous, non-aqueous or combination solvent which may be used during the oxidation processing in a manner that will subsequently be discussed. Specifically, solubilization of the ozone creates an ozonated solvent. Under most applications, the solvent is aqueous. A non-aqueous solvent is utilized when the use of such a solvent would provide a synergistic oxidation effect in combination with solubilized ozone in acting on a contaminant substrate. The contacting process chamber 14 is designed in a conventional manner. The contacting process chamber 14 may include appropriately designed contacting tanking or length of piping which may or may not be outfitted with baffles, gas absorber packing or a tortuous path for maximizing contacting. The contacting process chamber 14 may also include a porous or turbine diffusion system, venturi-type valves, Mazzei injection systems, a spinning disk contactor, hydrovac, etc. A venturi-type injection system is the preferred design for the contacting process, although other systems could be utilized without departing from the spirit of the present invention.

The contacting process chamber 14 functions to optimize the mass transfer of ozone from the gas to the liquid phase by thinning the liquid interfacial film to produce a gas to liquid ratio of approximately less than 1, introducing ozone gas to the liquid in the smallest attainable bubble sizes, maximizing the surface area for contacting, optimizing contactor hydrodynamics, etc. As stated previously, a venturi-type system is preferred for the contacting process. A venturi device has a narrowing orifice which causes an increase in pressure and flow rate of a fluid passing through the device. The compression of the fluid results in increased turbulence, increased number of bubbles and reduced bubble size. These factors provide an optimized transfer of ozone from the gas to liquid phases, if so required.

As discussed previously, the contacting process requires a solvent for solubilizing the ozone. This solvent is used by the system 10 and make-up solvent 16 must be introduced into the system 10. The make-up solvent is introduced in necessary amounts of aqueous, non-aqueous, or combination solvent to replace the solvent consumed by the system 10. The make-up solvent 16 may be stored in a holding tank 48 and is supplied to the contacting process chamber 14 or oxidation processing chamber 18 through a series of valves 50, 52, and 72. Flow of the make-up solvent is enhance by the provision of pump 49 positioned between the make-up solvent 16 and valve 50, and pump 51 positioned between valve 52 and valve 72. Pump 51 may be optional, since gravity may provide sufficient force to feed the make-up solvent to the contacting process chamber 14 and the oxidation chamber 18.

The solubilized ozone produced during the contacting process may follow a variety of paths. Some of the materials may be passed to a waste line 56 for treatment by the solvent/water treatment system 58 in a manner that will subsequently be discussed. The materials may also be recycled back to the feed line 60 for the make-up solvent via valve 61.

Similarly, waste gases are passed to a waste line 62 for treatment by the gas treatment system in a manner that will be discussed in greater detail below. Flow of waste from the contacting process chamber 14 is controlled by a series of valves 61, 66, 68, and 70. Handling of the components contained in the waste streams is dependent on the contaminants present in the stream. For instance, the liquids could be treated with flocculent to float liquid and solid contaminants to the top of the liquid for removal by skimming. Solid wastes may be removed by precipitation and/or filtration. Oily wastes may be removed by oil/water separation. In summary, numerous separation technologies, or technology combinations such as, ion exchange, biofiltration, flocculation, filtration, distillation, and adsorption, could be applied, while remaining within the spirit of the present invention.

The flow of materials from the contacting process chamber 14 is controlled by monitoring a variety of variables in an attempt to optimize the system. Specifically, the contacting system is designed to maximize the concentration of ozone transferred from the gas to the liquid phase. The temperature, flow rate, oxidation potential, and ozone concentration may be monitored to determine criteria for releasing the solution to the oxidation processing chamber 18. The release criteria is dependent on system applications. When values for the release criteria have been met, a relay is triggered to open an actuated valve 66 to release the solution to the oxidation process.

When the actuated valve 66 is released, the material contained in the contacting process chamber 14 is passed to the oxidation processing chamber 18. If required, the contacting processing chamber 18 may be drained through valves 66 and 61 for disposal, treatment or recycling. The contaminated object(s) are then treated by oxidation processing while within the oxidation processing chamber 18. Oxidation processing may either be batch processing, semi-continuous processing, or continuous processing.

For example, when the present system is used for showering humans or washing dishes, the oxidation processing would most likely take place in a batch processing mode; that is, only one individual is likely to be taking a shower and one load of dishes is washed at a time. In contrast, oxidation processing would likely be continuous or semi-continuous when foodstuff is being treated; that is, the foodstuff would likely be passed through the oxidation processing chamber on a conveyor while the oxidation processing continuously takes place.

Once the ozonated solvent is released from the contacting process chamber 14 and/or direct ozone via valve 44, enhancer 20, and substrate contaminant(s) (e.g., showering individual, dirty dishes, fruit, vegetables, meats, etc.) have been introduced to the oxidation processing chamber 18, oxidation processing may commence. The oxidation processing may be conducted at low temperatures, ranging from approximately 33°–110° F. In addition to the materials supplied from the contacting process chamber, as well as the ozone and enhancer previously discussed, make-up solvent 16 may be fed to the oxidation processing chamber 18 via valves 50, 52, and 72. As stated previously, the enhancer 20 includes any and all components which contribute oxidizing characteristics to effect controlled or uncontrolled reaction with the substrate contaminant(s).

The oxidation processing may involve oxidation by ozone or any other oxidant. Ozonation reactions may occur by dipole reactions such as the Criegee mechanism for reaction with unsaturated bonds. In addition, ozonation reactions may also occur from ozone acting in the role of an electrophilic agent, such as by reacting with electron donor groups such as OH, $NH_2$, etc. Ozonation reactions may also occur via nucleophilic reaction with electron deficit sites. Oxidation mechanisms would include any reaction that produces ozone, the hydroxyl radical, ozonide ion, or any other oxidatively reactive species via controlled or uncontrolled reaction means.

Oxidation processing produces waste which may be recycled and/or vented from the system in a variety of manners. Waste component handling is based on process knowledge or analytical results. The waste stream may contain solid, liquid, and gaseous components. Handling of the components contained in the waste stream is dependent on the contaminants present in the stream. For instance, the liquid could be treated with flocculent to float liquid and solid contaminants to the top of the liquid and removed by skimming. Solid wastes may be removed by precipitation and/or filtration. Oily wastes may be removed by oil/water separation. In summary, numerous separations technologies, such as, ion exchange, biofiltration, flocculation, filtration, distillation, and adsorption, could be applied.

The waste gases are treated by a gas treatment system 64. The waste gases are transmitted to the gas treatment system by waste gas lines 62 and 74 and valves 68 and 70. The gas treatment system 64 treats vented gases from the contacting process chamber 14 and/or the oxidation processing chamber 18. Generally, the only gas to be destructed and/or treated is ozone. The gas treatment system 64 may first utilize high efficiency particulate air (HEPA) filters to remove particulate and other suspended solid contaminants from the waste gas. The gas treatment system 64 may then separate the produced gases and feeds ozone to the ozone destruction unit 76 which vents 78 the gas. Ozone destruction may be accomplished in a variety of manners, such as, contacting the ozone with sodium thiosulfate, dilution, catalytic or thermal destruction, contacting the ozone with activated carbon or natural rubber, copper, manganese containing filtration systems, etc. Any condensed gas is returned via waste line 80 for treatment by the solvent/water treatment system as discussed later.

Liquid waste coming from the gas treatment system 64, the contacting process chamber 14 and the oxidation processing chamber 18 may then be fed to the solvent/water treatment system 58 via pump 82 and valves 84, 86, 88, 90, and 92, or fed by valves 84, 86, 88, and 92 directly to drain 94. The purpose of the solvent/water treatment system is to reclaim the aqueous, non-aqueous, or combination solvent for reuse. If the solvent is not desired for reuse, it may be treated and disposed through drain 94. If on the other hand the user desires to recycle the solvent, the waste is treated at the solvent/water treatment system 58, the water obtained from the treatment may be drained 94 or transported back via valve 96 and feed line 60 to the make-up solvent 16 feed line.

As one of skill in the art will appreciate, the present invention is provided with a wide variety of valves which control the flow of materials throughout the system. The valves are selectively opened or closed to the extent necessary to optimize the system. If the system is used for applications requiring a continuous steady state operation, the valves could be manually operated; that is, the valves would be set at their optimum position and left in that position. If on the other hand the system is consistently changing, it might be advantageous to utilize an automated computer control system to manage the status of the valves. In either case, the valves are designed to allow a user to selectively control the elements of the system in any manner he or she may deem appropriate.

The present invention finds applications in a wide variety of industries. For instance, the present system can be utilized in a portable or non-portable configuration for laundry, showering, dishwashing, pool or spa treatment, processing of slaughtered meat, floating or sinking raw fruit/vegetable processing, washing storage, disinfection, or primary or secondary packaging, remediation of soil/water, wood, pulp and paper processing, cleaning and sterilization of barnyard or dairy barn components, animals or resultant manure or other wastes, as an alternative to processes which use caustics, chlorinated compounds or any other Resource Conservation and Recovery Act (RCRA) hazardous compound to bleach, clean, disinfect, brighten or remove organic or non-organic containing contaminants within or on substrate surfaces.

Among the advantages of the present system is its ability to work at low temperatures. The present invention also discharges or vents a very limited amount of hazardous chemical or biological agents and treatment may result in coagulation of contaminants for easier removal via separation processing. In addition, the system may precipitate metals and does not produce trihalomethanes or other chlorinated organics. Further, the present invention makes organics more biodegradable and there is no storage or handling of strong oxidants. The process also requires lower doses of oxidant versus alternate process utilized to achieve similar results.

Process benefits include cleaning, decontaminating, purifying, brightening, bleaching, sanitizing, sterilization and/or disinfection of the contaminated object(s) or solution being treated. Configuration benefits include closed or open loop operation; non-venting/non-discharging or limited venting/discharging of residual contaminants; batch, semi-continuous, or continuous operation; and no or limited fouling of system components, even after long term operation. Oxidation mechanism benefits include oxidant residuals reacting with contaminant constituents or reverting back to oxygen. The elimination of power results in elimination of oxidant production.

With regard to the application of the present process and system in laundering applications, considerable cost savings are achieved while a product equal to, or better than, conventional laundering processes is produced. This is a result of the ability of the present invention to recycle water, clean with no or reduced souring steps and less rinsing, use lower temperature water (60°–130° F.) and reduce chemical use.

As to application of the present process and system to showering, ozone effectively kills bacteria which is often not attacked by conventional soap and water methods. Additionally, the ability of the present invention to recycle water and save water resources makes it especially attractive in confined environments such as ships, submarines, space stations, hospitals and nursing homes. The closed loop nature also significantly reduces the spread of viruses, disease and other illnesses. The ozone also deodorizes individuals exposed to it in accordance with the present invention.

Application of the present invention to meat, fruit and vegetable processing effectively kills all bacteria and viruses, without the need for chlorine or hydrogen peroxide treatment of the foodstuff. In fact, ozone treatment is substantially more effective than prior processes in its ability to decontaminate foodstuff.

The present invention can also be used in other agriculture applications such as biocide misting, storage environment control, packing, washing, control of mold, mildew and growth of microbial or fungal surface spores.

While various preferred embodiments have been shown and described, it will be understood that there is no intent to limit the invention by such disclosure or to require a system that includes all components to achieve desired processing results, but rather, is intended to cover all modifications and alternate constructions falling within the spirit and scope of the invention as defined in the appended claims.

We claim:

1. A system for enhanced contaminant destruction through the use of oxidation processing, comprising:

means for oxidation processing including a contacting process chamber where ozone is solubilized into a solvent to create ozonated solvent and an oxidation processing chamber where a target substrate is treated, wherein the contacting process chamber is coupled to the oxidation processing chamber to selectively supply ozonated solvent to the oxidation processing chamber;

means for controlling the supply of oxygen to an ozone generator, wherein the ozone generator is coupled to the contacting process chamber and the oxidation processing chamber, and the ozone generator generates ozone which is selectively supplied to the contacting process chamber and the oxidation processing chamber;

means for treating resultant gas and liquid streams produced in the means for oxidation processing, the means for treating including means for selectively processing solvent produced in the contacting process chamber and the oxidation processing chamber and means for selectively processing ozone produced in the contacting process chamber and the oxidation processing chamber; and, means for managing the selective supply of ozone to the contacting process chamber and the oxidation processing chamber, the selective processing of solvent and the selective processing of ozone.

2. The system according to claim 1, wherein the means for controlling the supply of oxygen includes an oxygen supply source selected from the group consisting of an air compressor, ambient air, recycled air and pure oxygen.

3. The system according to claim 1, wherein the means for controlling the supply of oxygen includes means for conditioning the oxygen.

4. The system according to claim 1, wherein the means for controlling the supply of oxygen includes an oxygen purifying unit.

5. The system according to claim 1, wherein the means for controlling the supply of oxygen includes an air compressor oxygen source, an ambient air oxygen source, a recycled air source and a pure oxygen source.

6. The system according to claim 1, wherein the means for selectively processing solvent includes a solvent/water treatment system which filters solvent from water, the solvent/water treatment system being coupled to a make-up solvent holding tank permitting the solvent reclaimed by the solvent/water treatment system to be reused.

7. The system according to claim 1, wherein the means for selectively processing ozone includes a gas treatment system which separates ozone from the gases produced in the contacting process chamber and the oxidation processing chamber.

8. The system according to claim 7, wherein the means for selectively processing ozone further includes an ozone destruction unit coupled to the gas treatment system.

9. The system according to claim 7, wherein the gas treatment system includes a filter for removing contaminants from gas.

10. The system according to claim 1, wherein the means for selectively processing ozone includes an ozone destruction unit coupled to a gas treatment system.

11. A system for enhanced contaminant destruction through the use of oxidation processing, comprising:

an oxidation processing system including a contacting process chamber where ozone is solubilized into a solvent to create ozonated solvent and an oxidation processing chamber where a target substrate is treated, wherein the contacting process chamber is coupled to the oxidation processing chamber to selectively supply ozonated solvent to the oxidation processing chamber;

an ozone generator coupled to the contacting process chamber and the oxidation processing chamber to selectively supply ozone;

a system for treating resultant gas and liquid streams produced in the oxidation processing system, the system for treating including:

a gas treatment system coupled to the contacting process chamber and the oxidation processing chamber to treat gases produced in the contacting process chamber and the oxidation processing chamber for destruction or reuse, wherein the gas treatment system is selectively in fluid communication with the contacting process chamber and the oxidation processing chamber; and, a solvent/water treatment system coupled to the contacting process chamber and the oxidation processing chamber to treat waste produced in the contacting process chamber and the oxidation processing chamber for reuse, wherein the solvent/water treatment system is selectively in fluid communication with the contacting process chamber and the oxidation processing chamber.

12. The system according to claim 11, wherein the ozone generator is coupled to means for controlling the supply of oxygen to an ozone generator.

13. The system according to claim 12, wherein the means for controlling the supply of oxygen includes an oxygen supply source selected from the group consisting of an air compressor, ambient air, recycled oxygen and pure oxygen.

14. The system according to claim 12, wherein the means for controlling the supply of oxygen includes means for conditioning the oxygen.

15. The system according to claim 12, wherein the means for controlling the supply of oxygen includes an oxygen purification unit.

16. The system according to claim 12, wherein the means for controlling the supply of oxygen includes an air compressor oxygen source, an ambient air oxygen source, a recycled oxygen source and a pure oxygen source.

17. The system according to claim 11, further including an ozone destruction unit coupled to the gas treatment system.

18. The system according to claim 11, further including an enhancer supply coupled to the contacting process chamber and the oxidation processing chamber to selectively supply enhancer to the contacting process chamber and the oxidation processing chamber.

19. The system according to claim 11, wherein the solvent/water treatment system is coupled to a make-up solvent holding tank permitting the solvent reclaimed by the solvent/water treatment system to be reused.

20. The system according to claim 11, wherein the gas treatment system includes a filter for removing contaminants from gas.

* * * * *